US009726635B2

(12) United States Patent
Kirk et al.

(10) Patent No.: US 9,726,635 B2
(45) Date of Patent: Aug. 8, 2017

(54) HYDROGEN QUALITY MONITOR

(71) Applicant: INTELLIGENT ENERGY LIMITED, Loughborough (GB)

(72) Inventors: Christopher James Kirk, Loughborough (GB); Simon Edward Foster, Loughborough (GB)

(73) Assignee: Intelligent Energy Limited, Loughborough (GB)

( * ) Notice: Subject to any disclaimer, the term of this patent is extended or adjusted under 35 U.S.C. 154(b) by 186 days.

(21) Appl. No.: 14/367,453

(22) PCT Filed: Dec. 19, 2012

(86) PCT No.: PCT/GB2012/053189
§ 371 (c)(1),
(2) Date: Jun. 20, 2014

(87) PCT Pub. No.: WO2013/093461
PCT Pub. Date: Jun. 27, 2013

(65) Prior Publication Data
US 2015/0346140 A1 Dec. 3, 2015

(30) Foreign Application Priority Data
Dec. 21, 2011 (GB) .................................. 1122035.7

(51) Int. Cl.
*G01N 27/417* (2006.01)
*H01M 8/0662* (2016.01)
(Continued)

(52) U.S. Cl.
CPC ......... *G01N 27/417* (2013.01); *B01D 53/228* (2013.01); *C01B 3/503* (2013.01);
(Continued)

(58) Field of Classification Search
CPC .......... G01N 27/417; C01B 3/56; C01B 3/58; C01B 3/503; B01D 53/228;
(Continued)

(56) References Cited

U.S. PATENT DOCUMENTS 5,763,113 A * 6/1998 Meltser ............... H01M 8/0447
429/432
7,175,928 B2 2/2007 Kuriiwa et al.
(Continued)

FOREIGN PATENT DOCUMENTS

EP 1 339 125 B2 10/2009
GB 2 478 190 A 8/2011
(Continued)

OTHER PUBLICATIONS

UK Patent Office Search Report dated Feb. 29, 2012, issued in GB Patent Application 1122035.7.
(Continued)

*Primary Examiner* — Natalie Huls
*Assistant Examiner* — Monica S Young
(74) *Attorney, Agent, or Firm* — Baker & Hostetler LLP

(57) ABSTRACT

A pair of fuel cells are configured as a hydrogen purity monitor. A first cell, acting as a reference cell, is configured to generate electrical current from the electrochemical reaction of hydrogen and oxidant and has a first fuel inlet configured to receive hydrogen from a first hydrogen source. A second fuel cell, acting as a test cell, is configured to generate electrical current from the electrochemical reaction of hydrogen and oxidant and has a second fuel inlet configured to receive hydrogen from a second hydrogen source. A control system is configured to apply an electrical load to each fuel cell and determine an electrical output of each fuel cell. The control system has a comparator for comparing the electrical outputs of the first and second fuel cells and a (Continued)

purity monitor output configured to give an indication of hydrogen purity based on an output of the comparator.

20 Claims, 2 Drawing Sheets

(51) Int. Cl.
- *H01M 8/04089* (2016.01)
- *H01M 8/04537* (2016.01)
- *C01B 3/56* (2006.01)
- *B01D 53/22* (2006.01)
- *C01B 3/50* (2006.01)
- *C01B 3/58* (2006.01)

(52) U.S. Cl.
CPC .................. *C01B 3/56* (2013.01); *C01B 3/58* (2013.01); *H01M 8/04089* (2013.01); *H01M 8/04537* (2013.01); *H01M 8/0662* (2013.01); *B01D 2256/16* (2013.01); *Y02E 60/324* (2013.01)

(58) Field of Classification Search
CPC .......... B01D 2256/16; H01M 8/04089; H01M 8/04537; H01M 8/0662; Y02E 60/50; Y02E 60/324
USPC ....................................................... 73/23.02
See application file for complete search history.

(56) References Cited

U.S. PATENT DOCUMENTS

| | | |
|---|---|---|
| 2003/0057109 A1 | 3/2003 | Wang et al. |
| 2003/0077492 A1* | 4/2003 | Kuriiwa ............ H01M 8/04089 429/411 |
| 2003/0175566 A1 | 9/2003 | Fisher et al. |
| 2004/0072046 A1 | 4/2004 | Schmidt |
| 2004/0247952 A1 | 12/2004 | Milacic et al. |
| 2006/0057034 A1 | 3/2006 | Speranza et al. |
| 2006/0078772 A1 | 4/2006 | Yu et al. |
| 2007/0243624 A1* | 10/2007 | Speranza .............. G01N 33/005 436/144 |
| 2007/0244601 A1* | 10/2007 | Speranza ........... G05B 23/0283 700/266 |
| 2007/0264546 A1* | 11/2007 | LaVen ............... H01M 8/04089 429/416 |
| 2009/0123294 A1 | 5/2009 | Dong et al. |
| 2010/0015039 A1* | 1/2010 | Doshi .................... B01J 8/0278 423/652 |
| 2010/0248050 A1* | 9/2010 | Hu .................... H01M 8/04626 429/428 |
| 2010/0254084 A1 | 10/2010 | Chen et al. |
| 2011/0262740 A1 | 10/2011 | Martin, III |
| 2012/0088171 A1* | 4/2012 | Edmiston ............ H01M 8/0488 429/429 |
| 2013/0084510 A1* | 4/2013 | Masui ............... H01M 8/04365 429/423 |

FOREIGN PATENT DOCUMENTS

| | | |
|---|---|---|
| GB | 2478829 | 9/2011 |
| JP | S56 47710 A | 4/1981 |
| JP | 2005-201639 A | 7/2005 |
| JP | 2006 059745 A | 3/2006 |
| JP | 2006059745 A * | 3/2006 |
| JP | 4659410 B2 | 3/2011 |
| WO | WO 2010/128555 A1 | 11/2010 |

OTHER PUBLICATIONS

SAES Micro Torr, "Hydrogen Ambient Temperature Purification", 2010.
International Search Report (PCT ISR) from International Patent Application No. PCT/GB2012/053189; mailed May 24, 2013.
Singapore Patent Application No. 11201403461V; Written Opinion; dated Mar. 27, 2015; 16 pages.

* cited by examiner

HYDROGEN QUALITY MONITOR

CROSS-REFERENCE TO RELATED APPLICATIONS

This application is a National Stage of International Patent Application No. PCT/GB2012/053189, filed Dec. 19, 2012 and claims priority to foreign application GB 1122035.7, filed Dec. 21, 2011, the contents of which are incorporated herein by reference in their entirety.

The present invention relates to apparatus and methods for monitoring the quality of a hydrogen supply.

The use of hydrogen as a fuel for the generation of electrical power in fuel cells is becoming of increasing importance. Purity of the hydrogen supply is important for optimal electrical power generation and for maintaining fuel cells using that hydrogen in optimal condition.

Currently, hydrogen used in fuel cell systems is often synthesized through the steam reforming of natural methane gas. Even where best quality practices are used, a number of contaminants may be present in the hydrogen fuel which are harmful to fuel cell operation. Although the harm is usually reversible, in the worst cases a high degree of contamination may be present including some compounds which may cause irreversible harm to the fuel cell.

It is an object of the invention to provide a convenient hydrogen quality monitor that is particularly, though not exclusively, suited to monitoring fuel supplies to fuel cells.

According to one aspect, the present invention provides a hydrogen purity monitor comprising:
  a first fuel cell configured to generate electrical current from the electrochemical reaction of hydrogen and oxidant, having a first fuel inlet configured to receive hydrogen from a first hydrogen source;
  a second fuel cell configured to generate electrical current from the electrochemical reaction of hydrogen and oxidant, having a second fuel inlet configured to receive hydrogen from a second hydrogen source;
  a control system configured to apply an electrical load to each fuel cell and determine an electrical output of each fuel cell, the control system including a comparator for comparing the electrical outputs of the first and second fuel cells; and
  a purity monitor output configured to give an indication of hydrogen purity based on an output of the comparator.

The hydrogen purity monitor may include a first hydrogen source comprising a hydrogen source of known purity. The known purity hydrogen source may be a hydrogen tank containing a reference gas. The hydrogen purity monitor may include a hydrogen purification device coupled between the first fuel inlet and the second fuel inlet to receive hydrogen from the second hydrogen source, and to provide hydrogen from the second hydrogen source to the first fuel inlet via the purification device as the first hydrogen source. The hydrogen purification device may include a catalytic purifier. The hydrogen purification device may comprise a palladium membrane. The comparator may be configured to determine a rate of change of voltage and/or current for each of the first and second fuel cells over a period of time. The second hydrogen source may be a steam reformer. The first fuel cell may comprise a plurality of series-connected fuel cells in a stack and/or the second fuel cell may comprise a plurality of series-connected fuel cells in a stack. The first fuel cell and the second fuel cell may form part of a single fuel cell stack. The first fuel cell and the second fuel cell may each be of the proton exchange membrane type. The hydrogen purity monitor may be integrated into a larger primary fuel cell stack.

According to another aspect, the present invention provides a method of monitoring hydrogen purity, the method comprising:
  supplying hydrogen fuel from a first hydrogen source to a first fuel cell configured to generate electrical current from the electrochemical reaction of hydrogen and oxidant;
  supplying hydrogen fuel from a second hydrogen source to a second fuel cell configured to generate electrical current from the electrochemical reaction of hydrogen and oxidant;
  applying an electrical load to each fuel cell and determining an electrical output of each fuel cell;
  comparing the electrical outputs of the first and second fuel cells; and
  providing an indication of hydrogen purity of one of the first and second hydrogen sources based on an output of the comparator.

Embodiments of the present invention will now be described by way of example and with reference to the accompanying drawings in which.

A convenient hydrogen purity monitoring system described here uses fuel cell technology in order to monitor hydrogen quality. The purity monitoring system provides contamination detection and can be used at hydrogen fuelling stations in order to assess fuel purity before it is delivered to customers. The purity monitoring system can also be used to monitor the hydrogen supply being fed to an operational fuel cell being used as an electrical power supply for a building or vehicle, for example (referred to herein as a primary fuel cell). The purity monitoring system can be used as a periodic testing system or as an "in-line", continuously-operating fuel monitor.

The purity monitoring system uses a configuration of at least two fuel cells in order to monitor hydrogen purity. An advantage of using fuel cells to perform the hydrogen purity monitoring is that it is relatively inexpensive compared to existing elemental analysis apparatus and methods. Another advantage of a fuel cell based purity monitoring system is that, by their very nature, the fuel cells performing the purity monitoring can readily be configured to be sensitive to exactly the same contaminants that are harmful to operation of a primary fuel cell stack with which the purity monitor can be associated.

Figure 1:
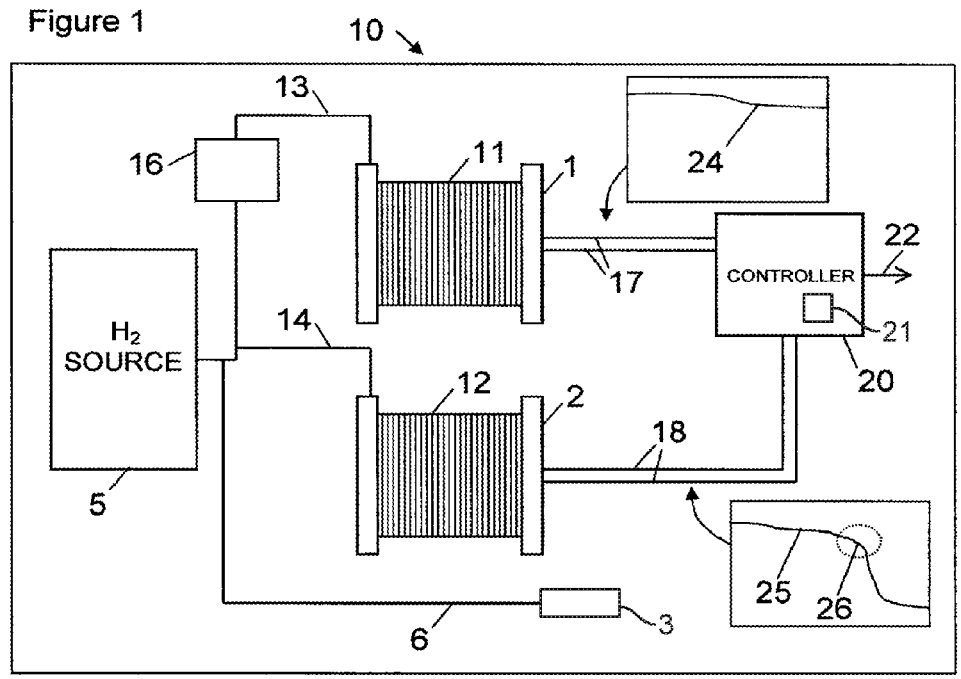
FIG. 1 shows a schematic diagram of a fuel cell based hydrogen quality monitor.

FIG. 1 shows a schematic diagram illustrating the principles of operation of a first configuration of hydrogen purity monitor 10. The purity monitor 10 includes a first fuel cell 11 and a second fuel cell 12. The first fuel cell 11 is a reference fuel cell and may further comprise a number of individual fuel cells disposed in series-connected configuration as a reference fuel cell stack 1. The second fuel cell 12 is a test fuel cell and may further comprise a number of individual fuel cells disposed in series connected configuration as a test fuel cell stack 2. The reference cell 11 has a fuel inlet 13 and the test cell 12 has a fuel inlet 14. In this arrangement, the fuel inlets 13, 14 are both supplied from a common hydrogen source 5. Hydrogen source 5 may be any form of hydrogen source including, but not limited to, any form of storage tank or vessel, a continuous piped supply, or a hydrogen generator such as a steam reforming system. The fuel inlet 13 is connected to the hydrogen source 5 by way of a purifier 16. The purifier 16 may be any form of filter capable of removing contaminants that would degrade the electrical performance of the reference fuel cell 11 and the test fuel cell 12. For example, any form of catalyst-activated purifier could be used. A preferred purifier is a palladium membrane. The purifier is preferably situated between the inlet 13 and the inlet 14 and the hydrogen source 5. Any suitable purifier or in-line gas purification method may be used, such as those based on an adsorption method using porous media or pressure swing adsorption. A range of possible hydrogen purifiers are commercially available, such as the MicroTorr® range from SAES Pure Gas Inc.

The hydrogen source 5 may also include an output 6 which is common to that supplied to fuel inlet 14, and which is coupled to a primary fuel cell stack 3, which can be a power source for electrical power generation.

The reference fuel cell 11 has an electrical output 17 and the test fuel cell 12 has an electrical output 18. Both electrical outputs 17, 18 are connected to a controller 20. Controller 20 is configured to apply an electrical load (not shown) to each of the fuel cells 11, 12 and to monitor the electrical outputs 17, 18 of the fuel cells 11, 12. The controller 20 also includes a comparator 21 which compares the electrical outputs 17, 18 of the fuel cells 11, 12. The controller 20 also provides a purity monitor output 22 configured to give an indication of hydrogen purity of the hydrogen source 5 based on an output of the comparator 21.

In use, the hydrogen source 5 supplies hydrogen fuel to the reference fuel cell 11 via the purifier 16, but supplies hydrogen fuel directly to the test fuel cell 12 without purification. By comparing performance metrics from the reference fuel cell 11 and from the test fuel cell 12, it is possible to test for the presence of contaminants in the hydrogen fed to the test fuel cell that are specifically harmful to fuel cell operation and which degrade electrical performance of the test fuel cell.

The controller 20 may be configured to carry out performance metrics continuously, periodically or intermittently. The performance metrics may include measuring fuel cell voltage at a constant output current and/or output current at a constant voltage for each of the reference cell and the test cell. As shown in the inset output graphs 24, 25, the rate of any voltage loss 26 in the test cell 12 compared to the reference cell 11 is related to the quantity and type of contamination in the hydrogen source fuel. The comparison with the reference cell 11 provides normalization of the measurements for environmental changes, such as temperature, humidity, air contamination and other factors that affect fuel cell performance.

Any suitable algorithm may be used for monitoring and comparing the relative performance of the reference and test cells 11, 12. An exemplary algorithm may determine a rate of change of voltage output for each of the reference and test cells and determine a purity level based on the difference in the respective rates of change. An exemplary algorithm may determine a purity level based on an absolute difference in the voltage outputs of the reference and test cells. The controller may be configured to trigger an alarm condition when the difference established exceeds a predetermined maximum, either transiently or over a defined period of time. A rate of change of voltage output may give an indication of the severity of contamination of the hydrogen supply.

Discrimination between different contaminants could be made by providing additional reference fuel cells that are each supplied with hydrogen from the hydrogen source 5 by way of different purifiers or contaminant filters, each filter configured to remove specific contaminants.

Alternatively, or in addition, discrimination between different contaminants could be made by providing further reference and test fuel cells with cells that have different catalysts, membranes or other features that are sensitive to different specific contaminants.

Figure 2:
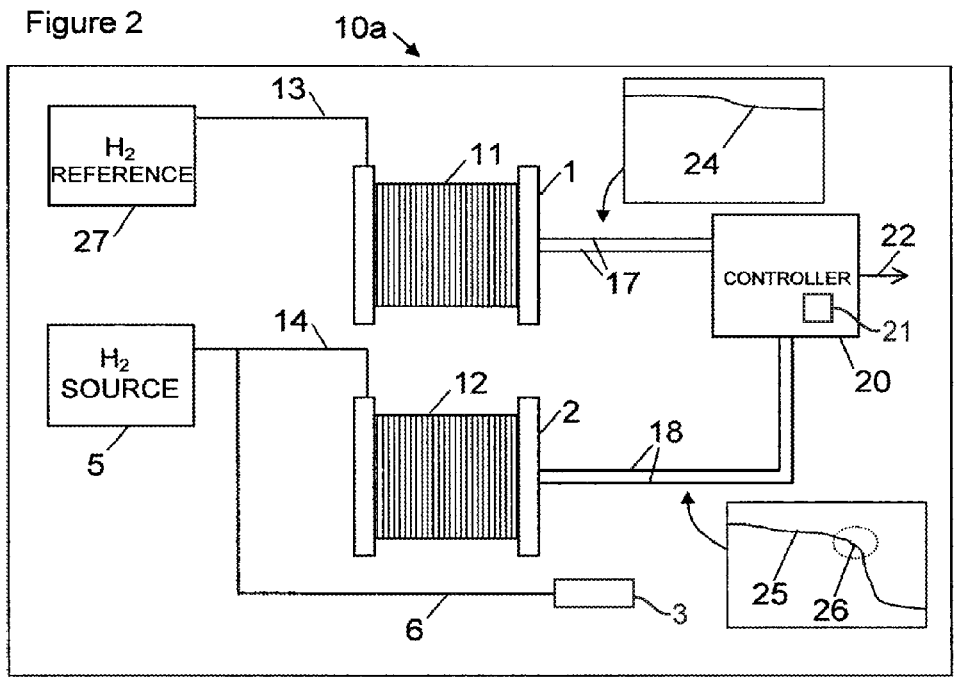
FIG. 2 shows a schematic diagram of an alternative fuel cell based hydrogen quality monitor.

In an alternative arrangement shown in FIG. 2, the hydrogen purity monitor 10a is provided with a separate high purity hydrogen source 27 instead of a purified supply from the main hydrogen source 5. In this arrangement, the high purity hydrogen source 27 can be a small storage vessel or tank of known high purity hydrogen reference gas, e.g. hydrogen of at least a known level of purity in a high integrity vessel. In other respects, the purity monitor 10a operates in the same way as the purity monitor 10 of FIG. 1.

The fuel cells of the hydrogen purity monitor 10, 10a are preferably of the proton exchange membrane type although other fuel cell types capable of generating electrical current from the electrochemical reaction of hydrogen and oxygen can be used.

The reference and test fuel cells 11, 12 may form part of one or more fuel cell stacks. In one arrangement, one or more series-connected reference cells may be coupled to one or more series-connected test cells in a single fuel cell stack. Appropriate voltage monitoring terminals can be provided in known manner in the stack from the relevant cells or groups of cells to provide the requisite outputs 17, 18. The stack would be provided with the necessary separate reference fuel supply for the reference cell or cells and test fuel supply for the test cell or cells. Integrating reference and test cells into the same stack could provide an advantage in that the ambient conditions (e.g. temperature, pressure, humidity etc) for operation of the reference and test fuel cells are more closely matched, thereby reducing any electrical output variation between the cells arising from a difference in ambient conditions.

The purifier 16 could also be integrated into the same fuel cell stack as the reference cells, e.g. by having a catalyst surface in a plate adjacent to the reference cell or cells and providing appropriate fluid flow ports for delivery of hydrogen so that the purifier and reference cell or cells are fluidically in series.

In another arrangement, the hydrogen purity monitor 10 or 10 a can be integrated into a primary fuel cell stack 3 that provides power to an external load, e.g. an automotive power unit. Appropriate voltage monitoring terminals can be provided in known manner in the primary fuel cell stack 3 from cells that are designated as the reference and test cells to provide the requisite outputs 17, 18. The primary fuel cell stack 3 would be provided with the necessary separate reference fuel supply for the reference cell or cells. The rest of the stack that serves as a primary stack power supply and the test cells would be provided with fuel from the source 5.

In another arrangement, the hydrogen purity monitoring system could be modular such that reference and/or test fuel cells and palladium membranes could be replaced on a regular basis either after a certain time period or after a contamination event.

The purity monitor may be configured to run for a set time period after a fuel delivery to the main fuel storage tank 5. Alternatively, a sample volume of a fuel delivery could be taken prior to filling the tank 5 to avoid dilution of contaminants in a fuel delivery. If the difference in voltage drop between the test and reference cells were to be above a preset value, the system may be configured to trigger a shut down in the delivery station and/or a primary fuel cell operating from a tank, or to trigger an alarm condition for a more detailed analysis of the fuel source.

After a contamination event, a test cell could be cleaned with purified hydrogen which could give some indication of the type of contamination. For example:

(i) an immediate improvement in test cell electrical output could indicate that the contamination event corresponded to concentration contamination (dilution) with a contaminant having no direct effect on the fuel cell catalyst but causing a reduction in hydrogen concentration;

(ii) an improvement over time in test cell electrical output could indicate that the contamination event corresponded to a reversible catalyst contamination e.g. with CO;

(iii) no or little improvement over time in test cell electrical output could indicate that the contamination event corresponded to an irreversible catalyst contamination e.g. with sulphur compounds.

The sensitivity of the hydrogen purity monitor to contamination of hydrogen can be improved if required. The impurity level within the hydrogen may be too small to be detectable using the apparatus of, e.g., FIG. 1 within a reasonable timescale. For example, sulphur-containing species may have a cumulative effect on the test fuel cell 12 and, broadly speaking, the impact on the test cell of exposure to 1 ppm impurities for 100 hours may be similar to that of 100 ppm for 1 hour. As such it could be beneficial if the impurities within the hydrogen are concentrated prior to feeding hydrogen to the test fuel cell 12. This can be achieved by using a cross-flow filtration type technique in the purifier 16 and reconfiguring the apparatus according to FIG. 3.

In a cross-flow filtration device, a feed flow is input to the filter and a proportion of this flow is able to pass through the filter membrane to form a filtered or purified output referred to as the permeate flow. Another proportion of the input flow passes along the upstream surface of the filter membrane, effectively washing the membrane, and is passed to a second output referred to as the retentate. Although cross-flow filtration is often used to reduce filter clogging by relying on the cross-flow to continuously clean the upstream face of the filter medium, in the apparatus described in FIG. 3 it has an additional benefit. In effect, the difference in impurity concentration between the purified permeate flow and the retentate flow has been increased, the impurities in the input flow having been concentrated into the retentate flow.

Figure 3:
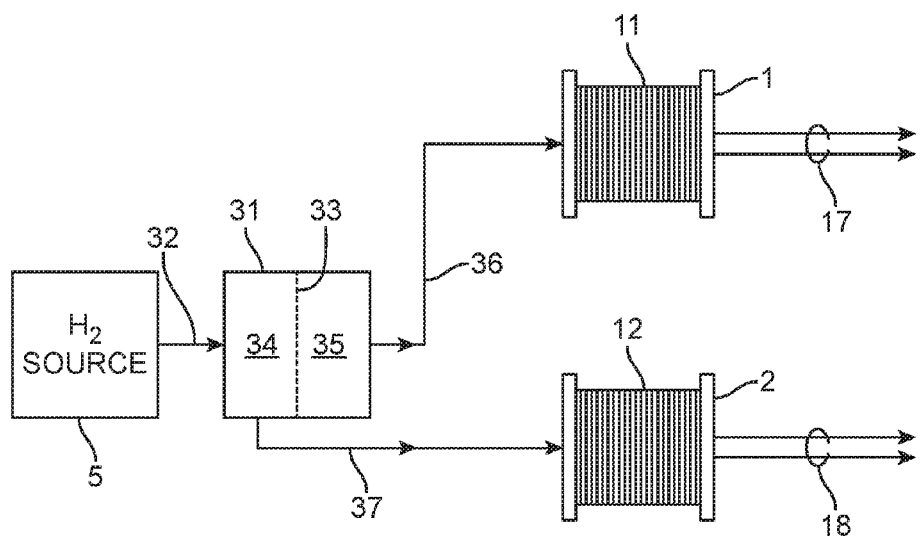
FIG. 3 shows a schematic diagram of an alternative fuel cell based hydrogen quality monitor.

With reference to FIG. 3, a hydrogen purity monitor 30 includes a purifier 31 with an input feed flow line 32 coupled to the hydrogen source 5, a membrane 33 having an upstream side 34 and a downstream side 35, a permeate flow line 36 in communication with the downstream side 35 of the membrane 33 and a retentate flow line 37 in communication with the upstream side 34 of the membrane 33.

The permeate flow line 36 is coupled to the reference fuel cell 11 and provides purified hydrogen thereto. The retentate flow line 37 is coupled to the test fuel cell 12 and provides hydrogen with concentrated impurities thereto. Thus, the difference in electrical outputs 17 and 18 is amplified according to the ratio of impurities found in the permeate and retentate flows.

In preferred examples, the purifier 31 comprises a palladium (Pd) membrane, sheet or film (which will be generally referred to herein as "membrane"). Hydrogen is able to permeate thin films of palladium. As such, when one side of the Pd membrane is exposed to a mixture of gas containing hydrogen, the hydrogen is able to permeate through the Pd membrane, but the other species do not. The hydrogen dissociates into atoms in order to diffuse through the membrane and then re-associates into molecules on the other side. This process can be accelerated or enhanced by maintaining an increased pressure differential across the membrane. The hydrogen passing through the membrane is the permeate, the hydrogen plus contaminants gas retained on the other side is the retentate. In order to maintain flux of hydrogen through the membrane, the high pressure feed side should preferably not become filled with the non-permeating species and the retentate flow assists in this. Other types of purifier 31 are possible, such as those with a polymer membrane.

By choosing a suitable retentate flow rate from the high pressure side of the membrane 33, a low level of impurities in the input feed flow (e.g. 0.1 ppm carbon monoxide) can be concentrated to 1 ppm or even 10 ppm in the retentate flow, by removal of hydrogen from the contaminated fuel stream to the permeate flow. Calibration techniques could be used to quantify the amount of impurity concentration effected by the cross-flow purifier 31 and thereby calibrate effective impurity levels in the feed flow based on the electrical outputs of the reference cell 11 and test cell 12.

Other embodiments are intentionally within the scope of the accompanying claims.

The invention claimed is:

1. A hydrogen purity monitor having a controller to process output voltages from at least two fuel cells utilizing the comparison result to indicate fuel purity comprising:
   a first fuel cell configured to generate electrical current from the electrochemical reaction of hydrogen and oxidant, having a first fuel inlet configured to receive hydrogen from a first hydrogen source;
   a second fuel cell configured to generate electrical current from the electrochemical reaction of hydrogen and oxidant, having a second fuel inlet configured to receive hydrogen from a second hydrogen source;
   a control system configured to apply an electrical load to each fuel cell and determine an electrical output of each fuel cell, the control system including a comparator for comparing the electrical outputs of the first and second fuel cells; and
   a purity monitor output configured to give an indication of hydrogen purity based on an output of the comparator;
   wherein the first hydrogen source comprises a reference hydrogen source of higher purity and the second hydrogen source comprises a test hydrogen source of lower purity; and
   wherein the first fuel cell and the second fuel cell are disposed within the hydrogen purity monitor such that the ambient conditions for operation of the first fuel cell and the second fuel cell are substantially the same;
   wherein the ambient conditions for operation of the first fuel cell and the second fuel cell that are substantially the same comprise at least one factor that affects fuel cell performance;
   wherein the at least one factor that affects fuel cell performance comprises at least one of humidity, temperature, pressure, and air contamination.

2. The hydrogen purity monitor of claim 1 wherein the first hydrogen source comprises a hydrogen source of known purity.

3. The hydrogen purity monitor of claim 2 in which the known purity hydrogen source is a hydrogen tank containing a reference gas.

4. The hydrogen purity monitor of claim 1 further including a hydrogen purification device coupled between the first fuel inlet and the second fuel inlet to receive hydrogen from the second hydrogen source, and to provide hydrogen from the second hydrogen source to the first fuel inlet via the purification device as the first hydrogen source.

5. The hydrogen purity monitor of claim 4 in which the hydrogen purification device includes a catalytic purifier.

6. The hydrogen purity monitor of claim 4 in which the hydrogen purification device comprises a palladium membrane.

7. The hydrogen purity monitor of claim 1 further including a hydrogen purification device coupled between the first fuel inlet and the second fuel inlet, the hydrogen purification device having a feed inlet and a permeate outlet and a retentate outlet,
the permeate outlet being coupled to the first fuel inlet to act as the first hydrogen source, and
the retentate outlet being coupled to the second fuel inlet to act as the second hydrogen source.

8. The hydrogen purity monitor of claim 7 in which the feed inlet of the hydrogen purification device is coupled to a common source of hydrogen.

9. The hydrogen purity monitor of claim 7 in which the hydrogen purification device comprises a palladium membrane.

10. A method of monitoring hydrogen purity, the method comprising:
supplying hydrogen fuel from a first hydrogen source to a first fuel cell configured to generate electrical current from the electrochemical reaction of hydrogen and oxidant;
supplying hydrogen fuel from a second hydrogen source to a second fuel cell configured to generate electrical current from the electrochemical reaction of hydrogen and oxidant;
applying an electrical load to each fuel cell and determining an electrical output of each fuel cell, wherein the applying is performed with the ambient conditions for operation of the first fuel cell and the second fuel cell being substantially the same;
comparing the electrical outputs of the first and second fuel cells; and
providing an indication of hydrogen purity of one of the first and second hydrogen sources based on the comparing of the electrical outputs of the first and second fuel cells;
wherein the first hydrogen source comprises a reference hydrogen source of higher purity and the second hydrogen source comprises a test hydrogen source of lower purity;
wherein the ambient conditions for operation of the first fuel cell and the second fuel cell that are substantially the same comprise at least one factor that affects fuel cell performance;
wherein the at least one factor that affects fuel cell performance comprises at least one of humidity, temperature, pressure, and air contamination.

11. The hydrogen purity monitor of claim 1 in which the comparator is configured to determine a rate of change of voltage, a rate of change of current, or both a rate of change of voltage and a rate of change of current for each of the first and second fuel cells over a period of time.

12. The hydrogen purity monitor of claim 1 in which the second hydrogen source is a steam reformer.

13. The hydrogen purity monitor of claim 1 in which the first fuel cell comprises a plurality of series-connected fuel cells in a stack, in which the second fuel cell comprises a plurality of series-connected fuel cells in a stack, or in which both the first fuel cell comprises a plurality of series-connected fuel cells in a stack and the second fuel cell comprises a plurality of series-connected fuel cells in a stack.

14. The hydrogen purity monitor of claim 1 in which the first fuel cell and the second fuel cell form part of a single fuel cell stack.

15. The hydrogen purity monitor of claim 14 integrated into a larger, primary fuel cell stack.

16. The hydrogen purity monitor of claim 1 in which the first fuel cell and the second fuel cell are each of the proton exchange membrane type.

17. The hydrogen purity monitor of claim 1 further comprising an alarm triggered when the comparator determines that a voltage output difference exceeding a predetermined limit has occurred.

18. The method of claim 10 wherein the at least one factor that affects fuel cell performance comprises at least temperature.

19. The method of claim 10 wherein the comparison of the electrical outputs of the first and second fuel cells is processed and used to indicate the ambient conditions that affect fuel cell performance.

20. The method of claim 10 wherein the first fuel cell and the second fuel cell form part of a single fuel cell stack.

* * * * *